United States Patent
Hodges, IV et al.

(10) Patent No.: US 10,285,842 B2
(45) Date of Patent: May 14, 2019

(54) SYSTEMS AND METHODS FOR INCREASING THE EFFECTIVENESS OF A MECHANICAL JOINT BRACE

(71) Applicants: Charles Edward Hodges, IV, Sumter, SC (US); Ethan Paul Castle, Centennial, CO (US)

(72) Inventors: Charles Edward Hodges, IV, Sumter, SC (US); Ethan Paul Castle, Centennial, CO (US)

(73) Assignee: THERAPEUTIC ENVISIONS, INC., Libertyville, IL (US)

( * ) Notice: Subject to any disclaimer, the term of this patent is extended or adjusted under 35 U.S.C. 154(b) by 565 days.

(21) Appl. No.: 14/829,867

(22) Filed: Aug. 19, 2015

(65) Prior Publication Data

US 2015/0351945 A1 Dec. 10, 2015

Related U.S. Application Data

(63) Continuation of application No. 14/329,318, filed on Jul. 11, 2014, now abandoned.

(60) Provisional application No. 61/928,847, filed on Jan. 17, 2014.

(51) Int. Cl.
*A61F 5/01* (2006.01)
*A61F 5/30* (2006.01)

(52) U.S. Cl.
CPC .......... *A61F 5/0123* (2013.01); *A61F 5/0104* (2013.01); *A61F 5/0106* (2013.01); *A61F 5/0109* (2013.01); *A61F 5/0125* (2013.01); *A61F 5/30* (2013.01); *A61F 2005/0137* (2013.01); *A61F 2220/0025* (2013.01)

(58) Field of Classification Search
CPC .. A61F 5/00; A61F 5/01; A61F 5/0106; A61F 5/0109; A61F 5/0118; A61F 5/0123; A61F 5/013; A61F 5/30; A61F 13/08
USPC ............................... 602/3, 20, 23, 60–63, 26
See application file for complete search history.

(56) References Cited

U.S. PATENT DOCUMENTS

| | | | |
|---|---|---|---|
| 2,238,804 A * | 4/1941 | Brown | A41B 11/10 2/240 |
| 3,318,305 A | 5/1967 | Schultz | |
| 4,089,064 A | 5/1978 | Chandler, Jr. | |
| 4,287,885 A | 9/1981 | Applegate | |
| 4,407,276 A | 10/1983 | Bledsoe | |
| 4,502,301 A | 3/1985 | Swallow et al. | |
| 4,624,247 A * | 11/1986 | Ford | A61F 5/0102 602/16 |
| 4,697,583 A | 10/1987 | Mason et al. | |

(Continued)

*Primary Examiner* — Keri J Nelson
(74) *Attorney, Agent, or Firm* — Kilpatrick Townsend & Stockton LLP

(57) ABSTRACT

According to the invention, a system for increasing the effectiveness of a mechanical joint brace worn by a user is disclosed. A sleeve may fit around, and to either side of, a user's joint. The sleeve may include a first portion which applies compressive pressure on a proximate side of the joint, a second portion disposed around the joint, and a third portion which applies compressive pressure on a distal side of the joint. A first set of pads may be disposed and compressed between at least a first portion of a mechanical joint brace worn over the sleeve and the proximate side of the joint. A second set of pads may be disposed and compressed between at least a second portion of the mechanical joint brace worn over the sleeve and the distal side of the joint.

20 Claims, 3 Drawing Sheets

(56) References Cited

U.S. PATENT DOCUMENTS

| | | |
|---|---|---|
| 5,016,621 A | 5/1991 | Bender |
| 5,575,010 A | 11/1996 | Chung |
| 5,836,904 A | 11/1998 | Cooper |
| 7,122,016 B1 | 10/2006 | DeToro et al. |
| 8,162,867 B2 * | 4/2012 | Nordt, III ............. A61F 5/0104 602/20 |
| 8,784,349 B1 * | 7/2014 | Nelson ................. A61F 5/0109 602/23 |
| 2004/0106887 A1 | 6/2004 | Schneider et al. |
| 2010/0082007 A1 | 4/2010 | Bobo |
| 2013/0296758 A1 | 11/2013 | Castillo |
| 2015/0202071 A1 | 7/2015 | Hodges et al. |

* cited by examiner

SYSTEMS AND METHODS FOR INCREASING THE EFFECTIVENESS OF A MECHANICAL JOINT BRACE

CROSS-REFERENCE TO RELATED APPLICATIONS

This application is a continuation application of U.S. patent application Ser. No. 14/329,318 filed Jul. 11, 2014, entitled "SYSTEMS AND METHODS FOR INCREASING THE EFFECTIVENESS OF A MECHANICAL JOINT BRACE," which claims priority to Provisional U.S. Patent Application No. 61/928,847 filed Jan. 17, 2014, entitled "SYSTEMS AND METHODS FOR SECURING ORTHOPEDIC AND OTHER BRACES," the entire disclosures of which are hereby incorporated by reference, for all purposes, as if fully set forth herein.

BACKGROUND OF THE INVENTION

This invention relates generally to orthopedic devices. More specifically the invention relates to assistive peripherals for orthopedic braces and prosthetic devices.

Joint injuries occur to hundreds of thousands in the United States every year. These joint injuries can involve the destabilization of the joint so severe as to induce damaging hypermobility. For example, hypermobility is a subsequent effect after a rupture of the commonly torn anterior cruciate ligament, also known as the ACL. Often, in addition to surgery and rehabilitation, mechanical joint braces, sometimes referred to as functional braces, are employed by those injured to aid in recovery from such injuries, by stabilizing the joint and preventing improper movement of the joint. As suggested by recent research, a knee that has undergone ACL reconstructive surgery has an increased risk for re-injury if the individual does not wear a functional knee brace. However, mechanical joint braces, even when recommended or prescribed by physicians may not provide all theoretically possible benefits for a number of reasons.

In particular, many mechanical joint braces do not provide a secure fit with the human body, or at least a particular user of the mechanical joint brace. This may result in some slippage of the brace in which the brace moves out of proper positioning on the braced joint. This may lead to potential injury thereafter due to undesired and detrimental forces applied to the body joint and its components due to the brace being located in the wrong position. At the very least, repositioning the brace may become a consistent inconvenience for the user. It is important that the hinge of the orthopedic device stay in the place of proper position on the joint as per a medical providers recommendation.

Widespread research has been conducted on the effects of mechanical joint braces and the experience of individuals wearing the brace. In addition to some findings indicating an increased risk of re-injury to some crucial ligaments if the applicable brace is not worn during post-surgical activities, other relevant findings have been recorded. A significant problem in regards to the braces was non-compliance due to brace discomfort, slippage, fit, and inhibition of performance. These findings include the detrimental effects of bracing on speed and agility, the abnormally excessive intramuscular pressure beneath some components of the knee brace that results in decreased local muscle blood flow and muscular oxygenation, the induction of premature muscle fatigue, and the inhibition or restriction of athletic performance.

Additionally, discomfort, irritation, injury, or deformation of the body may occur due to the fit and wear of the brace on the user. In particular, circulation in the braced area may be reduced due to the brace being tightened so that it maintains its position as well as possible, and muscles in the area may become misshapen at the areas where straps, the frame of the brace, or other securing mechanisms are employed. Lastly, a user may wear the brace less than they should because of the aforementioned issues (referred to as non-compliance by user), further increasing the opportunity for the joint to be reinjured.

Embodiments of the invention provide solutions to these and other problems.

BRIEF DESCRIPTION OF THE INVENTION

In one embodiment, a system for increasing the effectiveness of a mechanical joint brace worn by a user is provided. The system may include a sleeve, a first set of one or more pads, and a second set of one or more pads. The sleeve may be configured to fit around, and to either side, of a joint of a user. The sleeve may include a first portion which may apply compressive pressure on a proximate side of the joint, a second portion which may be disposed around the joint, and a third portion which may apply compressive pressure on a distal side of the joint. The first set of one or more pads may be coupled with the first portion of the sleeve, and be configured to be disposed and compressed between at least a first portion of a mechanical joint brace worn over the sleeve and the proximate side of the joint. The second set of one or more pads may be coupled with the third portion of the sleeve, and be configured to be disposed and compressed between at least a second portion of the mechanical joint brace worn over the sleeve and the distal side of the joint.

In another embodiment, a system for increasing the effectiveness of a mechanical joint brace worn by a user is provided. The system may include a sleeve, a first set of one or more pads, and a second set of one or more pads. The sleeve may be configured to fit around, and to either side, of a joint of a user. The sleeve may include a first portion which may apply compressive pressure on a proximate side of the joint, and a second portion which may apply compressive pressure on a distal side of the joint. The first set of one or more pads may be coupled with the first portion of the sleeve, and be configured to be disposed and compressed between at least a first portion of a mechanical joint brace worn over the sleeve and the proximate side of the joint. The second set of one or more pads may be coupled with the second portion of the sleeve, and be configured to be disposed and compressed between at least a second portion of the mechanical joint brace worn over the sleeve and the distal side of the joint.

In another embodiment, a system for increasing the effectiveness of a mechanical joint brace worn by a user is provided. The system may include a first sleeve, a second sleeve, a first set of one or more pads, and a second set of one or more pads. The first sleeve may apply compressive pressure on a proximate side of the joint. The second sleeve may apply compressive pressure on a distal side of the joint. The first set of one or more pads may be coupled with the first sleeve, and be configured to be disposed and compressed between at least a first portion of a mechanical joint brace worn over the first sleeve and the proximate side of the joint. The second set of one or more pads may be coupled with the second sleeve, wherein the second set of one or more pads is configured to be disposed and compressed between at least a second portion of the mechanical joint brace worn over the second sleeve and the distal side of the joint.

BRIEF DESCRIPTION OF THE DRAWINGS

The present invention is described in conjunction with the appended figures.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood by those skilled in the art that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, various structures, devices, processes, and techniques may be shown without unnecessary detail in order to avoid obscuring the embodiments. Additionally, any specific detail discussed with regard to one embodiment may or may not be present in all possible versions of that embodiment, and may or may not be present in all possible version of other embodiments described herein.

Figure 1A:
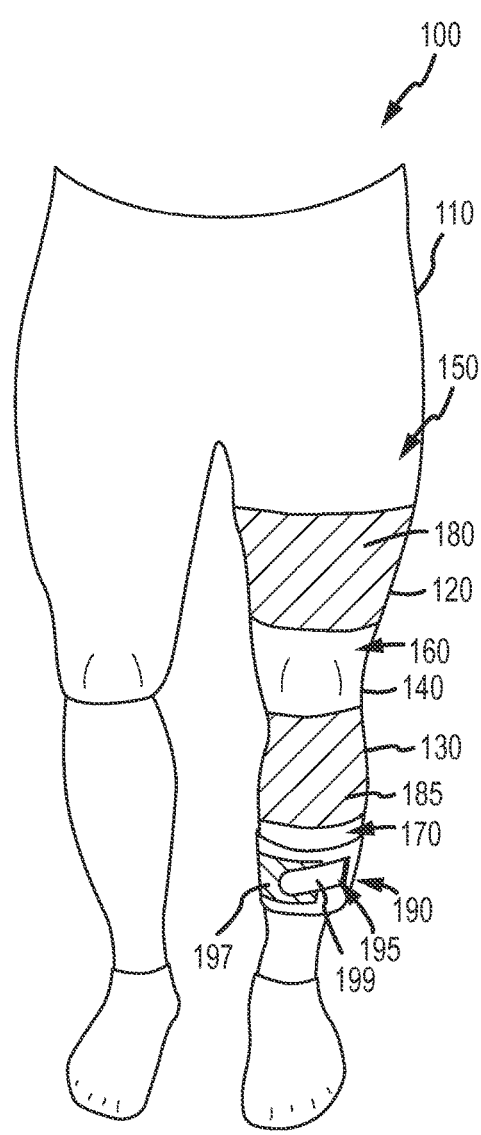
FIG. 1A is a front view of one system for increasing the effectiveness of a mechanical joint brace located at the knee joint of a user.
Figure 1B:
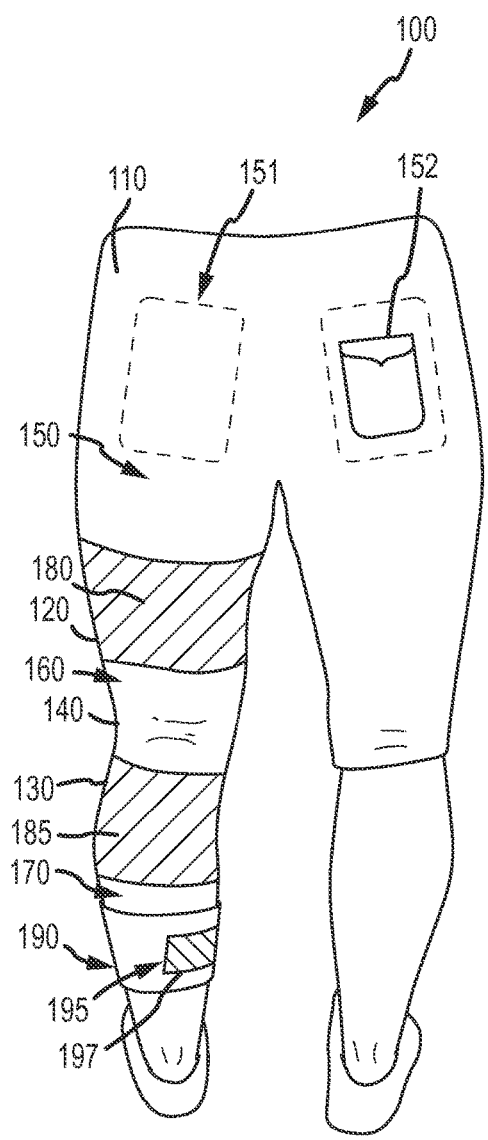
FIG. 1B is a back view of the system of FIG. 1A.

Turning now to FIGS. 1A & 1B, a system 100 for increasing the effectiveness of a mechanical joint brace worn by a user is shown. FIG. 1A shows a front view, while FIG. 1B shows a back view. In this specific example, system 100 is for use at the knee joint, but in other embodiments, other joints may employ an embodiment of the invention. Merely by way of example, an ankle joint, a hip joint, a shoulder joint, an elbow joint, or a wrist joint may also benefit from embodiments of the invention. Additionally, other areas of the body may also benefit from variations of the embodiments described herein. Merely by way of example, spinal and back areas, including the neck, may also benefit from embodiments of the invention.

System 100 may include a sleeve 110, a first set of one or more pads 120, and a second set of one or more pads 130. Though in this example sleeve 110 is shown as a pair of pants with one leg longer than the other, other forms of clothing may include sleeve 110 which is disposed over the relevant joint and surrounding areas of the user. When referred to herein, a "sleeve" is the portion of system 100 which is employed at, and in the vicinity of, the relevant joint. Thus, the "sleeve" may be the sleeve of a shirt, a leg of a pair of pants, the portion of a sock around the ankle, or some other portion of clothing which is located at a joint area. Merely by way of example, a pair of pants with equal length legs, a pair of shorts with equal or unequal length legs, a sock, a shirt with equal or unequal length arms, or a piece of clothing which covers some other portion of the body may be employed.

Sleeve 110 may be configured to fit around, and to either side, of joint 140 of a user. Sleeve 110 may include a first portion 150 which may apply compressive pressure on a proximate side of joint 140, a second portion 160 which may be disposed around joint 140, and a third portion 170 which may apply compressive pressure on a distal side of the joint. Note that second portion 160 may also apply a compressive pressure to the joint itself. Sleeve may be made from such material, and with a certain tailoring relative to the user (i.e., size, shape) that the compressive effect on the underlying areas is achieved. Such compressive pressure may provide other health benefits to the joint area, including increased blood flow, increased skin temperature, increased local perfusion and venous return.

In some embodiments, for example those embodiments which are implemented via a pair of pants, additional mechanisms for securing the sleeve to the user may be provided. For example, belt loops may be provided, or a waistband portion of the sleeve may be elongated (upwards toward the chest), and folded over to provide additional compression above the hips, therefore assisting in keeping the sleeve in place on the user. Straps such as suspenders may provide additional support, or sleeve 110 may be incorporated in larger pieces of clothing which cover more of the user's body, thereby providing additional support and securing of sleeve 110 on the body (i.e., sleeve 110 may be incorporated in a full body suit or "onesy." A strap may also be provided at relevant areas (i.e., the waistband in pant embodiments) to assist in supporting sleeve 110.

First set of one or more pads 120 may be coupled with first portion 150 of sleeve 110 in any number of manners. In some embodiments, the pads may be coupled with the exterior of sleeve 110, while in other embodiments the pads may be disposed within various layers of sleeve 110. In some embodiments, the pads may be disposed on the interior of sleeve 110. Any combination of the above may also be employed. First set of pads 120 may include any number and/or shape of pads. In some embodiments the placement and shape of pads will be such that the padded areas match the locations on which a mechanical joint brace contacts the user. In some embodiments, at least some portion of the padding may completely encircle the proximate side of joint 140. In these or other embodiments, at least some portion of the padding may not completely encircle the proximate side of joint 140. In some embodiments, any particular portion of the padding may be between 0.1 and 2 inches thick, or between 0.25 and 0.75 inches thick, in an uncompressed state. Any specific distance between these ranges may also be employed, or some thickness greater than the described ranges. As will be discussed below, first set of pads 120 may be configured to be disposed and compressed between at least a first portion of a mechanical joint brace worn over sleeve 110 and the proximate side of joint 140.

Second set of one or more pads 130 may likewise be coupled with third portion 170 of sleeve 110 in any number of matters. In some embodiments, the pads may be coupled with the exterior of sleeve 110, while in other embodiments the pads may be disposed within various layers of sleeve 110. In some embodiments, the pads may be disposed on the interior of sleeve 110. Any combination of the above may also be employed. Second set of pads 130 may include any number and/or shape of pads. In some embodiments the placement and shape of pads will be such that the padded areas match the locations on which a mechanical joint brace contacts the user. In some embodiments, at least some portion of the padding may completely encircle the proximate side of joint 140. In these or other embodiments, at least some portion of the padding may not completely encircle the proximate side of joint 140. In some embodiments, any particular portion of the padding will be between 0.25 and 0.75 inches thick in an uncompressed state. As will be discussed below, second set of pads 130 may be configured to be disposed and compressed between at least a second portion of a mechanical joint brace worn over sleeve 110 and the distal side of joint 140.

In various embodiments the composition of the padding may differ. In some embodiments, all or at least a portion of the padding may be a lightweight porous material, a gel, air pockets, and/or layers of material or fabric. In some embodiments, certain padding areas may be composed of one material, while others may be composed of a different material.

In some embodiments, system 100 may include a first fastening system 180 disposed on an exterior of sleeve 110 over at least a portion of first set of pads 120, and a second fastening system 185 over at least a portion of second set of pads 130, which are both configured to couple with a third fastening system disposed on an interior of the mechanical joint brace. In the embodiment shown, first fastening system 180 and second fastening system 185 are one half of a hook and loop fastening system, where the corresponding half is the third fastening system on the interior of the mechanical joint brace. In other embodiments, other types of fastening systems may be employed, including for example, buttons, snaps, and ties.

System 100 may also include a fold-over portion 190 at a distal end of sleeve 110. Fold-over portion 190 may be turned inside out at the distal end of sleeve 110 and thereafter be disposed over at least a portion, or potentially all, of the mechanical joint brace as will be discussed below. Fold-over portion 190 may include a fastening system 195 configured to tighten fold-over portion 190 around the mechanical joint brace. In this embodiment, fastening system 195 includes a hook and loop system 197 on the interior of sleeve 110, and a strap 199 with a corresponding hook and loop system to allow for tightening. In other embodiments, other types of fastening systems may be employed, including for example, buttons, snaps, and ties.

In some embodiments, additional padding 151 may be incorporated into the clothing for sports or other operational use purposes. For example, additional padding 151 may include padding on the buttocks area of pants as shown in the figures. Likewise, utilitarian pockets 152 may be provided in various locations.

Figure 2A:
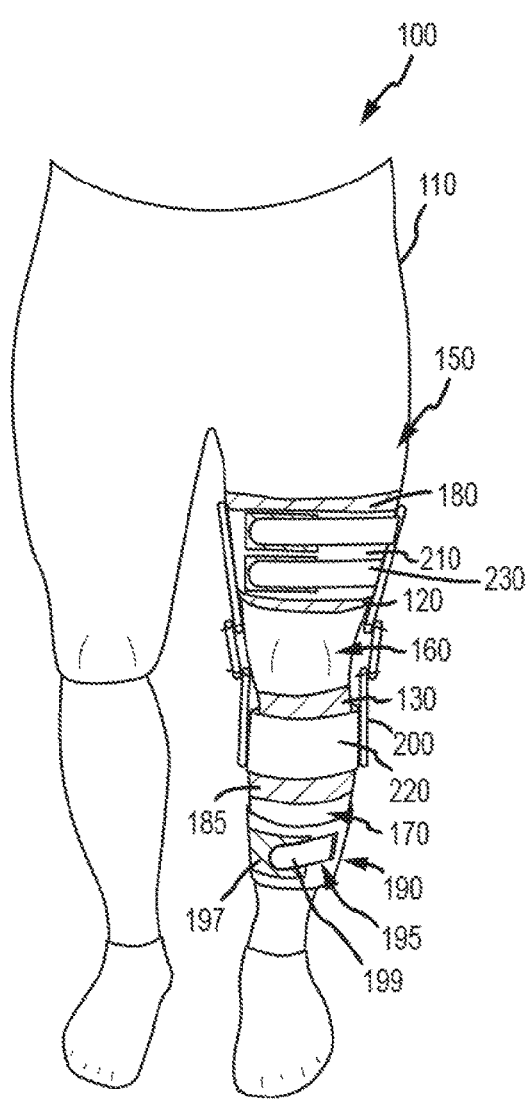
FIG. 2A is front view of the system of FIG. 1A with a mechanical joint brace disposed over the knee joint.
Figure 2B:
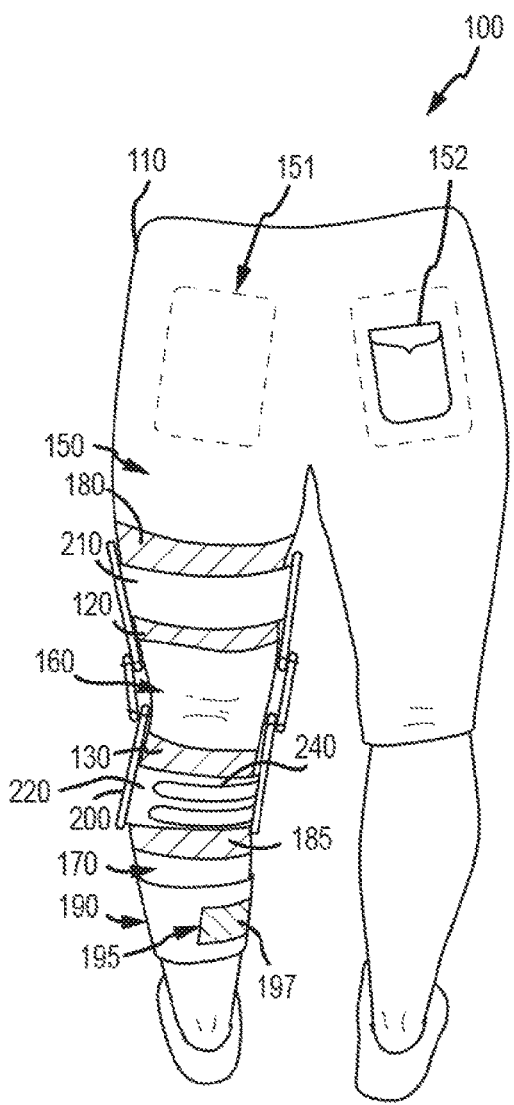
FIG. 2B is a back view of the system of FIG. 2A.

FIGS. 2A & 2B show a front and rear view of system 100 from FIGS. 1A & 1B with a mechanical joint brace 200 disposed over joint 140. A proximate portion 210 of brace 200 is coupled with the user over the proximate/first portion 150 of sleeve 110, while a distal portion 220 of brace 200 is coupled with the user over the distal/third portion 170 of sleeve 110. When fastening mechanisms 230, 240 of brace, shown here as hook and loop assisted straps, are tightened, proximate portion 210 of brace 200 compresses first set of padding 120 on sleeve 110, and distal portion 220 of brace 200 compresses second set of padding 130 on sleeve 110. As sleeve 110 is compression fitted onto user, the placement of brace 200 is made more secure than if padding 120, 130 and/or sleeve 110 were not present.

By disposing padding 120, 130 between brace 200 and the body of the user, pressure exerted by brace 200 on the user may be decreased. Padding 120, 130 may act much like a spring washer, decreasing and distributing the load of fastening mechanisms 230, 240 to a greater portion of the user's body, while increasing the stability of the brace at the location it is affixed to the user. Because slippage of brace 200 is reduced, irritation at the location of the brace may also be reduced. The padding may also reduce muscle deformation over the period of brace 200 usage. Finally, the compressive nature of sleeve 110 may assist in increasing blood flow to the joint area.

Figures 3A, 3B:
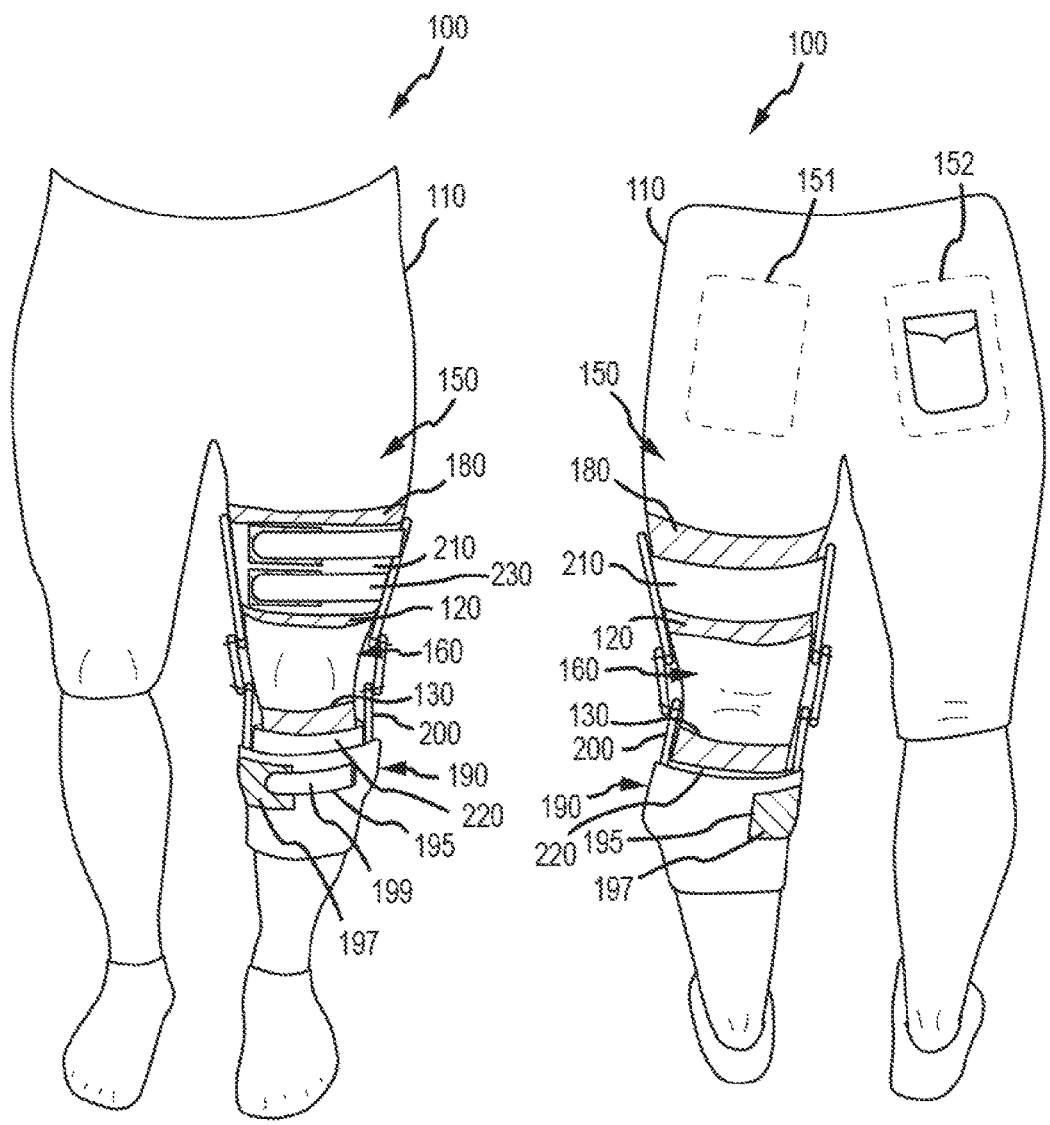
FIG. 3A is a front view of the system of FIG. 2A, with a fold-over portion of the system disposed over a portion of the mechanical joint brace.
FIG. 3B is a back view of the system of FIG. 3A.

FIGS. 3A & 3B show fold-over portion 190 pulled up and over distal portion 220 of brace 200. When fastening mechanism 195 is tightened, fold-over portion 190 further inhibits movement or migration of brace 200. Though shown here as only covering a portion of brace 200, in other embodiments, fold-over portion 190 could cover more or the entirety of brace 200. One or more additional fastening mechanisms may also be provided on fold-over portion at various locations to further assist in inhibiting movement or migration of brace 200, and to secure fold-over portion 190 over brace 200. For example, a fastening mechanisms could be located on fold-over portion 190 at the proximate end of brace 200, the middle of brace 200, and/or the distal end of brace 200.

A number of variations and modifications of the various embodiments discussed herein can also be used within the scope of the invention. For example, sleeve 110 may be located at a place on the user's body at which a prosthetic device or limb is employed. Padding in sleeve 110 may assist in providing better coupling of the prosthetic to the user, as well as increased comfort.

The invention has now been described in detail for the purposes of clarity and understanding. However, it will be appreciated that certain changes and modifications may be practiced within the scope of the appended claims.

What is claimed is:

1. A method for increasing the effectiveness of a mechanical joint brace worn by a user, wherein the method comprises:
disposing a sleeve over a limb of a user such that:
a first portion of the sleeve applies compressive pressure to the limb on a proximate side of a joint of the limb, wherein the first portion of the sleeve includes a first set of one or more pads at least partially encircling the limb on the proximate side of the joint;
a second portion of the sleeve is disposed around the joint; and
a third portion of the sleeve applies compressive pressure to the limb on a distal side of the joint, wherein the third portion of the sleeve includes a second set of one or more pads at least partially encircling the limb on the distal side of the joint;
disposing and tightening a mechanical joint brace over the sleeve such that:
a first portion of the mechanical joint brace compresses the first set of one or more pads of the sleeve between the first portion of the mechanical joint brace and the limb on the proximate side of the joint; and
a second portion of the mechanical joint brace compresses the second set of one or more pads of the sleeve between the second portion of the mechanical joint brace and the limb on the distal side of the joint.

2. The method for increasing the effectiveness of a mechanical joint brace worn by a user of claim 1, wherein disposing and tightening the mechanical joint brace over the sleeve comprises:
coupling a first portion of a first hook and loop fastening system on an interior of the first portion of the mechanical joint brace with a second portion of the first hook and loop fastening system on an exterior of the first portion of the sleeve; and
coupling a first portion of a second hook and loop fastening system on an interior of the second portion of the mechanical joint brace with a second portion of the second hook and loop fastening system on an exterior of the third portion of the sleeve.

3. The method for increasing the effectiveness of a mechanical joint brace worn by a user of claim 2, wherein:
the second portion of the first hook and loop fastening system is disposed on top of the first set of one or more pads; and
the second portion of the second hook and loop fastening system is disposed on top of the second set of one or more pads.

4. The method for increasing the effectiveness of a mechanical joint brace worn by a user of claim 1, wherein the method further comprises:
turning a distal end of the sleeve inside out and covering at least a portion of the mechanical joint brace with the distal end of the sleeve.

5. The method for increasing the effectiveness of a mechanical joint brace worn by a user of claim 4, wherein the method further comprises:
tightening a fastening mechanism on the inside of the distal end of the sleeve after the distal end of the sleeve has been turned inside out, wherein the fastening mechanism is exposed once the distal end of the sleeve has been turned inside out.

6. The method for increasing the effectiveness of a mechanical joint brace worn by a user of claim 5, wherein tightening the fastening mechanism comprises:
affixing a strap having a hook and loop fastening system to the inside of the distal end of the sleeve, wherein the inside of the distal end of the sleeve is exposed once the distal end of the sleeve has been turned inside out.

7. The method for increasing the effectiveness of a mechanical joint brace worn by a user of claim 1, wherein disposing the sleeve over the limb of the user comprises:
putting on a pants like compressive garment.

8. The method for increasing the effectiveness of a mechanical joint brace worn by a user of claim 1, wherein disposing the sleeve over the limb of the user comprises:
putting on a shirt like compressive garment.

9. The method for increasing the effectiveness of a mechanical joint brace worn by a user of claim 1, wherein:
the second portion of the sleeve applies compressive pressure direct to the joint.

10. The method for increasing the effectiveness of a mechanical joint brace worn by a user of claim 1, wherein the method further comprises:
turning a proximate end of the sleeve inside out for at least some portion of the proximate end.

11. A method for increasing the effectiveness of a mechanical joint brace worn by a user, wherein the method comprises:
disposing a sleeve over a limb of a user such that:
a first portion of the sleeve applies compressive pressure on a proximate side of a joint of the limb, wherein the first portion of the sleeve includes a first set of one or more pads at least partially encircling the limb on the proximate side of the joint; and
a third portion of the sleeve applies compressive pressure on a distal side of the joint, wherein the third portion of the sleeve includes a second set of one or more pads at least partially encircling the limb on the distal side of the joint;
disposing and tightening a mechanical joint brace over the sleeve such that:
a first portion of the mechanical joint brace compresses the first set of one or more pads of the sleeve between the first portion of the mechanical joint brace and the limb on the proximate side of the joint; and
a second portion of the mechanical joint brace compresses the second set of one or more pads of the sleeve between the second portion of the mechanical joint brace and the limb on the distal side of the joint.

12. The method for increasing the effectiveness of a mechanical joint brace worn by a user of claim 11, wherein disposing and tightening the mechanical joint brace over the sleeve comprises:
coupling a first portion of a first hook and loop fastening system on an interior of the first portion of the mechanical joint brace with a second portion of the first hook and loop fastening system on an exterior of the first portion of the sleeve; and
coupling a first portion of a second hook and loop fastening system on an interior of the second portion of the mechanical joint brace with a second portion of the second hook and loop fastening system on an exterior of the third portion of the sleeve.

13. The method for increasing the effectiveness of a mechanical joint brace worn by a user of claim 11, wherein the method further comprises:
turning a distal end of the sleeve inside out and covering at least a portion of the mechanical joint brace with the distal end of the sleeve.

14. The method for increasing the effectiveness of a mechanical joint brace worn by a user of claim 13, wherein the method further comprises:
tightening a fastening mechanism on the inside of the distal end of the sleeve after the distal end of the sleeve has been turned inside out, wherein the fastening mechanism is exposed once the distal end of the sleeve has been turned inside out.

15. The method for increasing the effectiveness of a mechanical joint brace worn by a user of claim 11, wherein the method further comprises:
turning a proximate end of the sleeve inside out for at least some portion of the proximate end.

16. A method for increasing the effectiveness of a mechanical joint brace worn by a user, wherein the method comprises:
disposing a sleeve over a limb of a user such that:
a first portion of the sleeve, which includes a first set of one or more pads, at least partially encircles the limb on the proximate side of a joint of the limb; and
a third portion of the sleeve, which includes a second set of one or more pads, at least partially encircles the limb on the distal side of the joint;
disposing and tightening a mechanical joint brace over the sleeve such that:
a first portion of the mechanical joint brace compresses the first set of one or more pads of the sleeve between the first portion of the mechanical joint brace and the limb on the proximate side of the joint; and a second portion of the mechanical joint brace compresses the second set of one or more pads of the sleeve between the second portion of the mechanical joint brace and the limb on the distal side of the joint.

17. The method for increasing the effectiveness of a mechanical joint brace worn by a user of claim 16, wherein disposing and tightening the mechanical joint brace over the sleeve comprises:

coupling a first portion of a first hook and loop fastening system on an interior of the first portion of the mechanical joint brace with a second portion of the first hook and loop fastening system on an exterior of the first portion of the sleeve; and coupling a first portion of a second hook and loop fastening system on an interior of the second portion of the mechanical joint brace with a second portion of the second hook and loop fastening system on an exterior of the third portion of the sleeve.

18. The method for increasing the effectiveness of a mechanical joint brace worn by a user of claim 16, wherein the method further comprises:

turning a distal end of the sleeve inside out and covering at least a portion of the mechanical joint brace with the distal end of the sleeve.

19. The method for increasing the effectiveness of a mechanical joint brace worn by a user of claim 18, wherein the method further comprises:

tightening a fastening mechanism on the inside of the distal end of the sleeve after the distal end of the sleeve has been turned inside out, wherein the fastening mechanism is exposed once the distal end of the sleeve has been turned inside out.

20. The method for increasing the effectiveness of a mechanical joint brace worn by a user of claim 16, wherein the method further comprises:

turning a proximate end of the sleeve inside out for at least some portion of the proximate end.

* * * * *